United States Patent [19]

Ezer et al.

[11] Patent Number: 4,616,025

[45] Date of Patent: Oct. 7, 1986

[54] THIAZOLIDINE DERIVATIVES, PROCESS FOR THE PREPARATION AND PHARMACEUTICAL COMPOSITIONS THEREOF

[75] Inventors: Elemer Ezer; Kalman Harsanyi; György Dományi; László Szporny; Judit Matuz; Béla Hegedüs; Katalin Pallagi; István Szabadkai; Peter Tétényi, all of Budapest, Hungary

[73] Assignee: Richter Gedeon Vegyeszeti Gyar RT, Budapest, Hungary

[21] Appl. No.: 590,486

[22] Filed: Mar. 16, 1984

[30] Foreign Application Priority Data

Mar. 16, 1983 [HU] Hungary .................. 888/83

[51] Int. Cl.[4] .................. C07D 277/10; C07D 277/18; A61K 31/425
[52] U.S. Cl. ..................... 514/342; 514/365; 514/370; 514/371; 546/280; 548/146; 548/193; 548/196; 548/198
[58] Field of Search .......... 548/196, 198, 146, 193; 546/280; 514/370, 371, 365, 342

[56] References Cited

U.S. PATENT DOCUMENTS 4,468,518  8/1984  Fujimoto .................. 548/342

FOREIGN PATENT DOCUMENTS 171986  10/1982  Japan ..................... 548/196
8023682  2/1983  Japan ..................... 548/146
8222886  12/1983  Japan ..................... 548/146

Primary Examiner—Robert Gerstl
Attorney, Agent, or Firm—Karl F. Ross; Herbert Dubno

[57] ABSTRACT

New thiazolidine compounds of the formula (I) having anti-ulcer activity are disclosed:

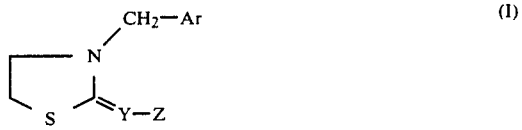

wherein

Ar is a 2-furyl or a phenyl, naphthyl or pyridyl group optionally substituted by one or more $C_{1-4}$-alkyl, $C_{1-4}$-alkoxy, halo-$C_{1-4}$-alkoxy, dihalomethyl, trihalomethyl, hydroxyl or nitro groups or by a group of the formula (II),

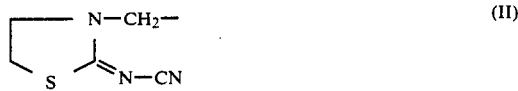

wherein Y is nitrogen or CH;

Z is cyano or carbamoyl if Y is nitrogen, and represents a nitro group if Y is CH.

Also disclosed are several processes for preparing the new compounds as well as pharmaceutical compositions and method of treatment employing same.

7 Claims, No Drawings

THIAZOLIDINE DERIVATIVES, PROCESS FOR THE PREPARATION AND PHARMACEUTICAL COMPOSITIONS THEREOF

This invention relates to new thiazolidine derivatives, a process for their preparation and pharmaceutical compositions containing them. More particularly, the invention concerns new thiazolidine derivatives of the formula (I)

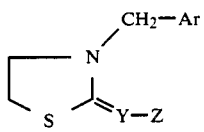
(I)

wherein
Ar is a 2-furyl or a phenyl, napthyl or pyridyl group optionally substituted by one or more of $C_{1-4}$-alkyl, $C_{1-6}$-alkoxy, halo-$C_{1-4}$-alkoxy, di- or trihalomethyl, hydroxyl or nitro or by a group of the formula (II),

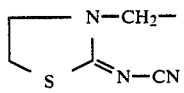
(II)

wherein
Y is nitrogen or CH;
Z is cyano or carbamoyl when Y is nitrogen, and is nitro when Y is CH.

The new compounds are valuable anti-ulcer agents, i.e. highly effective in the treatment of gastrointestinal ulcers. A process for the preparation of these compounds as well as pharmaceutical compositions containing them as active ingredient are also within the scope of the invention.

The compounds of the formula (I) have a high therapeutical importance, since the number of people suffering from gastic and duodenal ulcer is continuously increasing both in absolute and in relative terms. Though there are numerous pharmaceuticals employed in the ulcus therapy, out of the 4,5-dihydrothiazoles until now merely the 4-aryl-4-hydroxy-4,5-dihydrothiazoles (U.S. Pat. No. 4,143,148), which are structurally substantially different from the instant compounds, have been reported to show anti-ulcer activity.

As to their action mechanism the known anti-ulcer agents are extremely manifold. The recently discovered histamine-$H_2$ antagonists, such as cimetidine (N-cyano-N'-methyl-N''-2-[(5-methyl-imidazole-4-yl)-methylthio]-ethyl-guanidine) form a uniform group and are characterized in that they inhibit the histamine-induced gastric acid secretion selectively. Of the tricyclic 6H-pyrido[2,3-b][1,4]benzodiazepines, pirenzepine, which is (5,11-dihydro-11-[(4-methyl-1-piperazinyl)-acetyl]-6H-pyrido[2,3-b][1,4] benzodiazepine-6-one is known as a material which inhibits the formation of ulcers to the same extent as atropine but is devoid of other anticholenergic effects (e.g. inhibition of peristalsis, accommodation disturbances of eye, inhibition of salivation). Various antacid materials which do not inhibit the overproduction of gastic acid, but rather bind the excess amount of acid have come also into general use.

The compounds of the formula (I) as defined hereinabove have a broad spectrum of activity and are therefore suitable for treating gastrointestinal ulcer resulting from various patomechanisms, and among others can successfully be employed even in the treatment of ulceration induced by non-steroidal antiinflammatory agents. Certain preferred representatives of these anti-ulcer compounds, e.g. 3-benzyl-2-cyano-imino-thiazolidine have the further essential advantage that, unlike many known histamine-$H_2$ receptor antagonists, they do not contain a functional group from which undesirable, cancerogenic N-nitroso compounds could be formed in the organism.

For the chemical classification of the new compounds according to the invention there are more alternative possibilities. According to the nomenclature of Chemical Abstracts these compounds can be considered as substituted carbonic acid derivatives, e.g. cyanamide, urea, etc. compounds, which contain a heterocyclic moiety as a substituent. On the other hand, there are compounds, for example those containing =C—$NO_2$ substituent in the 2-position, in which the heterocycle should be considered as the basic structural element, to which for example the above side-chain is attached as a substituent. For the sake of unformity we classified all compounds of the formula (I) as a thiazolidine derivative, clearly indicating the unsaturated character of the side-chain in the 2-position (e.g. cyanoimino, nitromethylene, etc.).

The compounds of the formula (I) as defined hereinbefore can be prepared by alternative methods:

(a) an N-substituted 1-amino-2-thiol-derivative of the formula (III)

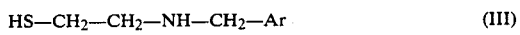
(III)

wherein Ar has the same meaning as defined above, is reacted with a compound of the formula (IV)

(IV)

wherein Y and Z are as defined above, and L is a leaving group, or (b) a 2-substituted thiazolidine derivative of the formula (V),

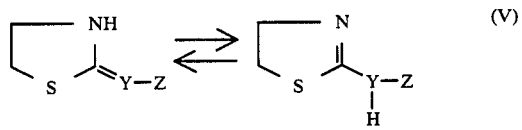
(V)

wherein Y and Z are as defined above, is N-alkylated with a compound of the formula (VI),

(VI)

wherein Ar is as defined above, and X is halogen or a reactive ester group, or (c) to prepare compounds of the formula (I), in which Y is nitrogen, Z is cyano and Ar is as defined above, a compound of the formula (VII),

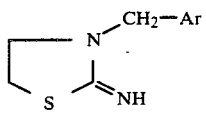

(VII)

wherein Ar is as defined above, is reacted with cyanogen bromide, or (d) is a compound of the formula (I), wherein Ar, Y and Z have the same meaning as defined above, a substituent is converted into another substituent within the definition given hereinabove, in a manner known per se.

Process (a) according to the invention is carried out in the presence of a solvent, the progress of the reaction can be monitored by observing gas evolution. As a solvent, depending on the solubility of the reactants employed, preferably water and optionally aqueous lower alcohols, acetone, ether, acetonitrile, hydrocarbons or chlorinated hydrocarbons can be used. The reaction temperature can be varied within wide limits, and is a function of the reactants and solvent employed. To ensure a suitable reaction speed the reaction is preferably carried out between about 40° and 80° C. The by-product formed in the reaction depends on the leaving group and preferably is methyl mercaptan which leaves the rection mixture in a vapor state, the desired product can easily be isolated from the reaction mixture, e.g. by filtration if the product is crystallized out, or by evaporating the reaction mixture.

The secondary mercaptoalkyl-arylmethyl-amines of the formula (III) used as a starting material can for example be prepared by reacting a corresponding oxo-compound (aldehyde or ketone) with an 1-amino-2-thiol compound and reducing the thiazolidine derivative obtained with a complex metal hydride (see J. Org. Chem. 27, 4712 [1963]).

The process (b) according to the invention is generally accomplished in an organic solvent, preferably methanol, ethanol, acetone, an ether, e.g. dioxane or acetonitrile, and as an acid binding agent for example alkali metal hydroxides, carbonates or alcoholates or organic bases, for example quaternary ammonium compounds can be employed. The reaction is generally carried out at the boiling temperature of the solvent employed; after filtering off the precipitated salt the product is isolated by crystallization or by evaporation of the reaction mixture and, if desired, is subjected to further purification by conventional methods.

When carrying out process (c) according to the invention the starting compound of the formula (VII) is preferably freshly set free from an acid addition salt thereof, which is more stable than the free base, and the base dissolved in an organic solvent is reacted with a bromocyanogen solution prepared from an aqueous solution of potassium cyanide with bromine, immediately before the reaction.

Process (d) relates to the conversion of a substituent of the compounds of formula (I) into another substituent within the definition given hereinabove. For example the Z cyano group can be hydrolyzed into a carbamoyl group, in an aqueous acidic medium. When reacting a compound of the formula (I), in which Z is cyano with an acid, for example hydrochloric acid in a non-aqueous medium, a separable iminochloride intermediate is obtained, from which the desired compounds of the formula (I), in which Z stands for carbamoyl, can be prepared by alkalization in an aqueous medium.

As a further example for converting certain substituents of the compounds of the formula (I) into other substituents the transformation of the optional substituents of the Ar group should be mentioned, which is performed by known methods. Thus the methoxy group in the compounds of the formula (I), in which Ar represents a phenyl group substituted with methoxy can be converted into a hydroxyl group by reacting the compound with borotribromide in an organic solvent and alkalizing the reaction mixture. Similarly, the hydroxyl group in the compounds of the formula (I) can be converted into other substituents within the definition given hereinbefore, by known methods.

A preferred representative of the compounds of formula (I) is 3-benzyl-2-cyanoimino-thiazolidine (compound A). Hereinbelow the results of the pharmacological tests performed with this compound will be summarized, it should, however, be noted that the other compounds of formula (I) also showed a significant activity.

The pharmacological activity of the new compounds has been investigated by the following methods:

Shay-ulcer

The method was first described by Shay et al in 1945 (Gastroenterology 56, 5–13, 1945). Female H-Wistar rats (120–150 g) were gasted for 24 hours. Water was allowed ad libitum. The pylorus of the animals was ligated in slight ether narcosis. The test drugs were administered during operation. 4 hours after treatment the animals were killed by an overdose of ether. The stomach was excised and cut along the large curvature. The volume and the pH of the contents were determined, in certain cases the HCl production was determined by titration.

Aspirin-induced stomach ulcer

It is known that the non-steroidal antiinflammatory agents induce gastointestinal ulceration to certain extent (Drugs and Peptic Ulcer, Ed. Pfeiffer, CRC Press, New York 1982). To test anti-ulcer compounds the so-called Aspirin-induced ulcer model is widely used. Female H-Wistar rats weighing 120–150 g each were fasted for 24 hours. Water was allowed ad libitum. The stomach ulcer was induced by oral administration of 100 mg/kg Aspirin (in Tween 80 suspension). The test drug was given simultaneously with the administration of Aspirin, orally. The animals were killed by an overdose of ether, 4 hours after treatment. The stomach was excised and cut along the large curvature. The contents were slightly washed and the haemorrhagic lesions in the glandular surface were counted. When evaluating the test results, the number of ulcers per stomach or the ulcer-free animals were determined.

Indomethacin-induced intestinal ulceration

Of the non-steroidal antiinflammatory agents indomethacin has not only a gastric-ulcer inducing side-effect but may also cause serious intestinal ulceration. Depending on the dose, the intestinal ulceration may be fatal, peritonitis due to intestinal perforations kills the animals.

(a) Indomethacin-induced fatal intestinal ulceration

Non-fasted, female H-Winstar rats, weighing 120–150 g each were treated orally with a 15 mg/kg dose of indomethacin (in Tween 80 suspension). The test materials were administered after the indomethacin administration, orally. Under these conditions it requires about 48 to 72 hours to detect intenstinal ulceration.

To evaluate the development of intestinal ulcers the so-called inflation technique by Ezer and Szporny (J. Pharm. Pharmacol. 27, 866 (1975)) was employed. By this method the progress of ulceration can be monitored quantitatively. The tensile strength of the intestinal wall expressed in mmHg weakens gradually parallel with the progress of ulceration.

(b) Indomethacin-induced non-fatal ulceration

Non-fasted H-Wistar rats weighing 120 to 150 g each were administered 7.5 mg/kg indomethacin orally, to induce non-fatal intestinal ulceration. 4, 24 and 48 hours, respectively, after the indomethacin treatment the animals were treated with the test material orally. The animals were killed 24 hours after the last treatment and 72 hours after the ulcer-induction performed with indomethacin, respectively. Ulceration was evaluated by the inflation technique.

Gastric necrosis induced by absolute alcohol

This method has been introduced by A. Robert (Gastoroenterology, 77, 43 (1979)) together with the term cytoprotection, Female, H-Wistar rats weighing 120 to 150 g each were fasted for 24 hours. Water was allowed ad libitum. The compounds to be tested were administered orally, 30 minutes prior to the administration of 0.5 ml of ethanol/100 g of body weight through a canula. Two hours later the animals were killed by overdosing ether. Stomachs were removed and opened along the major curvature. The lesions induced by ethaol were located at the corpus of the stomach as multiple linear hemorrhagic bands of necrotic tissue. Lengths of lesions were measured in millimeters (Derelanko and Long, Proc. Soc. Exp. Biol. and Med. 166, 394 (1981)), and the length of the average lesions per stomach was given. Degree of the cytoprotection was expressed in % related to the control.

Our studies carried out with the above-described pharmacological methods showed that 3-benzyl-2-cyanimininothiazolidine (Compound A), which is a preferred representative of the compounds of formula (I) according to the invention, proved a very effective anti-ulcer compound in each pharmacological test. This compound inhibits the gastric acid secretion in Shay rats in a low dose ($ED_{50}=5.3$ mg/kg i.p.). The aspirin-induced stomach ulcers were also inhibited by the compound A administered simultaneously per os ($ED_{50}=2.1$ mg/kg p.o.). Compound A is effective also in the absolute alcohol necrosis test recently introduced by Robert et al (Gastroenterology, 77, 433-443 (1979)). It should in particular be noted that simultaneous administration of compound A inhibits the indomethacin-induced intestinal ulceration. This result is important since cimetidine, one of the most effective anti-ulcer agents, cannot inhibit intestinal ulceration induced by indomethacin (Ezer and Szporny, J. Pharm. Pharmacol 33, 250-251 (1981; Der Soldato et al, Brit. J. Pharmacol. 67, 33-37 (1979); G. L. Kauffman et al, Proc. Soc. Exp. Biol. 161, 512-14 (1970). This is supported by the clinical results of Mitchell and Sturrock (Brit. Med. J. 284, 731 (1982)) which showed that a simultaneous administration of cimetidine and indomethacin result in perforation in rheumatic patients simultaneously suffering from ulceration. Anticholinergic compounds (e.g. Propanthelin, Gastrixon) cannot prevent indomethacin-induced intestinal ulceration either.

The results of the above studies are summarized in Tables 1 to 7. In the headings the following abbreviations are used:

n=number of the test animals
b.w.=bodyweight
t.s.=tensile strength.

TABLE 1

The gastric acid secretion inhibiting effect of Compound A in Shay-rats (pylorus ligation: 4 hours)

| Treatment | n | Dose mg/kg i.p. | Acid secretion μmol HCl/ 100 g b.w. | Inhibition in % | Remark |
|---|---|---|---|---|---|
| Control | 20 | — | 429 | — | |
| Compound A | 5 | 1.25 | 436 | ∅ | |
| Compound A | 10 | 2.5 | 358 | 17 | |
| Compound A | 10 | 5.0 | 301 | 30 | $ED_{50} = 5.3$ |
| Compound A | 20 | 10.0 | ∅ | 100 | |
| Compound A | 5 | 25.0 | ∅ | 100 | |

TABLE 2

The gastric acid secretion inhibiting effect of Compound A administered in various routes (Shay-rats, 4 hours)

| Route of administration | n | Dose mg/kg | Gastric acid secretion ml/100 g, b.w. | vol. inhibition | pH |
|---|---|---|---|---|---|
| 15 min. prior to operation i.p. | 5 | 10 | 2.5 | 42% | 3.7 |
| 15 min prior to operation s.c. | 5 | 10 | 2.8 | 35% | 1.5 |
| 15 min prior to operation p.c. | 5 | 10 | 2.3 | 47% | 4.1 |
| Control | 5 | — | 4.3 | — | 1 |

TABLE 3

Inhibition of aspirin-induced gastric ulcers by parallel treatment with the compound A

| Treatment | n | Dose mg/kg p.o. | Number of ulcers/stomach | Ulcer inhibition % | Ulcer-free animals % |
|---|---|---|---|---|---|
| Aspirin (control) | 20 | 100 | 15.7 ± 3.0 | — | 0 |
| Aspirin + compound A | 10 | 100 + 1.5 | 9.5[xx/] | 40 | 0 |
| Aspirin + compound A | 17 | 100 + 3.0 | 6.8[x/] | 57 | 23 |
| Aspirin + compound A | 17 | 100 + 6.0 | 4.7[x/] | 71 | 29 |
| Aspirin + compound A | 14 | 100 + 12.0 | 2.2[x/] | 86 | 66 |
| Aspirin + compound A | 17 | 100 + 25.0 | 2.3[x/] | 85 | 41 |

[xx/]$p < 0.05$
[x/]$p < 0.1$
$ED_{50} = 2.1$

TABLE 4

Dose-dependent inhibition of indomethacin-induced intestinal ulceration by simultaneous administration of Compound A

| Treatment | n | Dose mg/kg p.o. | T.s. of intestinal wall 72 hours after treatment in mm Hg | Intestinal wall resistency in % of normal | Remark |
|---|---|---|---|---|---|
| Untreated | 30 | — | 231 ± 5 | 100 | x/p < 0.01 |
| Indomethacin | 16 | 15 | 46 ± 12 | 20 | related to indomethacin group |
| Indomethacin + compound A | 10 | 15 + 15 | 120 ± 20 | 52 | |
| Indomethacin + compound A | 10 | 15 + 25 | 192 ± 18 | 83$^{x/}$ | |
| Indomethacin + compound A | 20 | 15 + 50 | 225 ± 6 | 97$^{x/}$ | $ED_{100} = 50$ |
| Indomethacin + cimetidine | 10 | 15 + 150 | 47 ± 25 | 21 | |
| Indomethacin + Na—salicylate | 10 | 15 + 25 | 132 ± 17 | 57$^{x/}$ | $ED_{100} = 50$ |
| Indomethacin + Na—salicylate | 10 | 15 + 50 | 231 ± 5 | 100$^{x/}$ | |

TABLE 5

The progress of indomethacin-induced (7.5 mg/kg p.o.) non-fatal intestinal ulceration in the case of cimetidine and compound A post-treatment

| Treatment 4, 24, 48 hours after indomethacin-treatment | n | Dose mg/kg p.o. | T.s. of intestinal wall 72 hours after indomethacin treatment (mm Hg) | Group |
|---|---|---|---|---|
| Untreated animals | 30 | — | 231 ± 5 | A |
| Indomethacin | 32 | 7.5 | 185 ± 11 | B |
| Indomethacin + Cimetidine | 12 | 7.5 + 3 × 50 | 184 ± 7 | C |
| Indomethacin + Cimetidine | 12 | 7.5 + 3 × 100 | 197 ± 10 | D |
| Indomethacin + Compound A | 10 | 7.5 + 3 × 25 | 176 ± 20 | F |
| Indomethacin + Compound A | 10 | 7.5 + 3 × 50 | 249 ± 4 | G |

A–B p < 0.05
B–C, D, F N.S.
B–G p < 0.01

TABLE 6

Cytoprotective effect of Compound A against gastric necrosis induced by absolute alcohol

| Treatment | n | Dose mg/kg p.o. | Length of average lesion (mm/stomach) | Cytoprotection (%) | Remark |
|---|---|---|---|---|---|
| Control | 112 | — | 82.4 ± 5 | — | |
| Compound A | 6 | 1.5 | 52.5 ± 19 | 37$^{x/}$ | |
| Compound A | 12 | 3.0 | 34.8 ± 10 | 58$^{x/}$ | $ED_{50} = 2.8$ |
| Compound A | 12 | 6.0 | 29.9 ± 9 | 64$^{x/}$ | |
| Compound A | 13 | 12.0 | 32.9 ± 5 | 60$^{x/}$ | |
| Compound A | 6 | 25.0 | 18.0 ± 8 | 78$^{x/}$ | |
| Cimetidine | 5 | 6.0 | 46.0 ± 10 | 44$^{x/}$ | |
| Cimetidine | 5 | 12.0 | 63.0 ± 18 | 24 | |
| Cimetidine | 10 | 25.0 | 55.0 ± 12 | 33 | $ED_{50}$ not calculable |
| Cimetidine | 15 | 50.0 | 34.0 ± 10 | 59$^{x/}$ | |
| Cimetidine | 12 | 100.0 | 47.0 ± 16 | 43$^{x/}$ | |

$^{x/}$p < 0.01 related to the control

The data in Table 1 show that compound A has a dose-dependent gastric acid secretion decreasing effect. It is very important that compound A effectively inhibits the gastric acid secretion also when administered orally as illustrated by the data obtained on Shay-rats and set forth in Table 2.

Compound A inhibits the formation of the aspirin-induced gastric ulceration when administered simultaneously, depending on the dose employed. Gastric ulcers induced by a 20 mg/kg oral dose of indomethacin are also effectively inhibited. The results are shown in Table 3.

In Table 4 the inhibition of fatal intestinal ulceration induced by a 15 mg/kg oral dose of indomethacin is illustrated.

Compound A shows a dose-dependent inhibiting effect on the intestinal ulceration induced by indomethacin (15 mg/kg p.o.). The results obtained in the so-called non-fatal intestinal ulceration model are deemed especially important. In these studies the treatment is started 4 hours after inducing ulceration with indomethacin (7.5 mg/kg p.o.). Accordingly, a post-treatment is carried out 4, 24 and 48 hours after indomethacin treatment. The data of Table 5 show that cimetidine and ranitidine are ineffective in this experiment, while compound A can normalize the tensile strength of the intestine wall depending on the dose employed.

Compound A is effective against the gastric necrosis induced by absolute alochol, too. According to the data set forth in Table 6 the cytoprotection is dose-dependent.

On the basis of the pharmacological data compound A has a wider spectrum of activity than for example cimetidine. It has a combined action mechanism, which is indicated by the fact that this compound is effective in three different ulcer models, characteristic of three distinctly different patomechanisms:

(1) aspirin-induced gastric ulcer model
(2) indomethacin-induced intestinal ulcer model
(3) absolute alcohol-induced gastric necrosis model.

Compound A has a good oral absorption as illustrated by the comparison of i.p., s.c. and p.o. data.

According to the first toxicological studies compound A has a high therapeutic index.

Toxicological studies

Compound A is insoluble in water, therefore for i.p. and oral administration a suspension of this compound in Tween 80 was employed. For intravenous administration the compound was dissolved in dimethyl formamide.

1. A 100 mg/kg dose results in sickness of the test animals but no death occurs (within 3 days).
2. After the administration of 250 mg/kg dose no death is observed within 2 weeks, while after the administration of a 1500 mg/kg i.p. dose the animals are dead in 30 minutes.
3. Oral administration of a 1500 mg/kg dose results in the death of 3 animals out of 10 within 24 hours, no further deaths are observed in the next week, the behavior and food consumption of animals are normal.

Further details of the invention are illustrated by the following examples, which do not limit the scope of our invention.

EXAMPLE 1

3-Benzyl-2-cyanimino-thiazolidine (a) To a boiling mixture of 1.27 g (10 mmoles) of 2-cyanimino-thiazolidine (2-thiazolidinylidene-cyanamide), 25 ml of acetone and 1.52 g of anhydrous potassium carbonate 1.3 ml (11 moles) of benzyl bromide are added dropwise. The mixture is boiled for 4 hours, the salt filtered off and the acetone solution is evaporated. The crystalline residue is triturated with ether and filtered to yield 2.03 g (93.5%) of the named compound, melting at 102° to 104° C. Recrystallization of the product does not alter the melting point.

Analysis for $C_{11}H_{11}N_3S$ (217.29): calculated: C 60.80, H 5.10, N 19.34, S 14.76%; found: C 60.98, H 5.02, N 19.57, S 14.96%.

IR spectrum (KBr): 2190 cm$^{-1}$ —C≡N 1570 cm$^{-1}$ =C=N— (broad).

NMR spectrum (CDCL$_3$): 3.38 ppm m(2) —S—CH$_2$— 3.85 ppm m(2) =N—CH$_2$— (heterocyclic) 4.65 ppm S(2) =N—CH$_2$— (phenyl) 7.38 ppm S(5) —Ar—H.

(b) 2.21 g (13.2 mmoles) of N-benzyl-cysteamine (boiling point: 90° C./0.2 mmHg) and 1.93 g (13.5 mmoles) of cyaniminodithiocarbonic acid dimethylester are boiled in 10 ml of ethanol. The intense gas evolution terminates in 15 minutes. The mixture is kept at 0° C. overnight, and is subsequently filtered to yield 2.57 g (89.6%) of the named compound, which has the same melting point and spectrum data as indicated under point (a) above. The product when admixed with the product of step (a) above does not give any melting point depression, and the two products cannot be distinguished by layer chromatography. Accordingly, the products prepared by two different processes both bear the benzyl group on the endocyclic nitrogen.

(c) To 2 ml of bromine 1 ml of water is added under vigorous stirring and cooling with salted ice, until there is a brown color. To the bromocyanogen solution obtained the solution obtained by extracting an aqueous solution of the base set free from 6.37 g (23.3 mmoles) of 3-benzyl-2-imino-thiazolidine hydrobromide with 30 ml of a 10% sodium hydroxide solution, with chloroform is added. The bi-phase reaction mixture is stirred for 10 hours, the phases are separated, the organic phase is evaporated, the residue is solidified by admixing with ether and the solid crude product is boiled with ethyl acetate. As a result, 3-benzyl-2-cyanimino-thiazolidine is dissolved. The ethyl acetate solution is partially evaporated to yield a crystalline product. 1.75 g (35%) of 3-benzyl-2-cyanimino-thiazolidine are obtained, melting at 100° to 101° C. The material which remains insoluble during the ethyl acetate extraction of the crude product essentially is the hydrobromide of the 3-benzyl-2-imino-thizaolidine starting material (1.97 g; 32.34%).

The 3-benzyl-2-imino-thiazolidine hydrobromide used as a starting material (melting point: 190° to 191° C.) is prepared by reacting 2-amino-thiazolidine with benzyl bromide in acetonitrile.

EXAMPLE 2

2-Cyanimino-3(4-chlorobenzyl)-thiazolidine 3,82 g (30 moles) of 2-cyanimino-thiazolidine, 4.9 g (30 mmoles) of 4-chlorobenzyl chloride and 4.3 g of anhydrous potassium carbonate are boiled in 100 ml of acetone for 5 hours. The inorganic salt is filtered off and the acetonic solution is evaporated. The residue is crystallized from 40 ml of isopropanol to yield 6.26 g (83%) of 2-cyanimino-3(4-chlorobenzyl)-thiazolidine, melting at 131° to 133° C. The product is isolated by filtration.

Analysis for $C_{11}H_{10}ClN_3S$ (251.74): calculated: C 52.48%, H 4.00%, N 16.69%; found: C 52.72%, H 4.18%, N 16.49%.

IR spectrum (KBr): 2185 cm$^{-1}$ —C≡N; 1560 cm$^{-1}$ =C=N—;

1092 cm$^{-1}$ —Ar—Cl.

NMR spectrum (CDCL$_3$+DMSO—d$_6$) 3.3 ppm m(2) —S—CH$_2$— 3.8 ppm m(2) =N—CH$_2$— (heterocycle) 4.50 ppm S(2) =N—CH$_2$—(C$_6$H$_4$—Cl) 7.12 ppm S(4) —Ar—H.

EXAMPLE 3

2-Cyanoimino-3-(3,4-dichlorobenzyl)-thiazolidine 3.82 g (30 mmoles) of 2-cyanimino-thiazolidine are reacted with 6 g (31 mmoles) of 3,4-dichlorobenzyl chloride as described in the previous Example, and the evaporation residue is recrystallized from 50 ml of ethanol to yield 6.8 g of 2-cyanimino-3-(3,4-dichlorobenzyl)-thiazolidine, melting at 130° to 132° C.

Analysis for $C_{11}H_9Cl_2N_3S$ (286.18): calculated: C 46.16%, H 3.17%, S 11.21%; found: C 46.12%, H 3.18%, S 11.22%.

IR spectrum (KBr): 2190 cm$^{-1}$—C≡N; 1570 cm$^{-1}$ =C=N—; 1060 cm$^{-1}$ —Ar—Cl.

NMR spectrum (CDCl$_3$): 3.4 ppm m(2) —S—CH$_2$— 3.7 ppm m(2) =N—CH$_2$— (heterocyclic) 4.56 ppm s(2) =N—CH$_2$—(3,4-dichlorophenyl) 6.9-7.5 ppm m(3) —Ar—H.

EXAMPLE 4

2-Cyanimino-3-(4-nitrobenzyl)-thiazolidine 2.54 g (20 mmoles) of 2-cyanimino-thiazolidine, 3.43 g of nitro-benzyl chloride and 2.95 g of anhydrous potassium carbonate are boiled in 80 ml of acetone for 6 hours. The salt formed is filtered off, the solution is evaporated and the residue is crystallized from 30 ml of acetonitrile. 3.66 g (70%) of 2-cyanimino-3-(4-nitrophenyl)-thiazoline are obtained, melting at 171° C.

Analysis for $C_{11}H_{10}N_4O_2S$ (262.29): calculated: C 50.37%, H 3.84%, N 21.36%; found: C 50.36%, H 3.94%, N 21.46%.

IR spectrum (KBr): 2190 cm$^{-1}$ —C≡N; 1575 cm$^{-1}$ =C=N—; 1505, 1343 cm$^{-1}$ —NO$_2$.

NMR spectrum (CDCl$_3$+DMSO—d$_6$): 3.4 ppm m(2) —S—CH$_2$—; 3.8 ppm m(2) =N—CH$_2$—; 4.65 ppm s(2) =N—CH$_2$—C$_6$H$_4$—p—NO$_2$; 7.35 ppm d (2) —Ar—H (2.6); 8.05 ppm d (2) —Ar—H (3.5);

EXAMPLE 5

2-Cyanimino-3-(2-hydroxyl-5-nitro-benzyl)-thiazolidine 3.82 g (30 mmoles) of 2-cyanimino-thiazolidine, 5.63 g (30 moles) of 2-hydroxy-5-nitro-benzyl chloride and 4.3 g of anhydrous potassium carbonate are boiled in 100 ml of acetone for 6 hours. The mixture is cooled and the precipitate is filtered off. 9.85 g of a crude material are obtained, which is then dissolved in 600 ml of hot water, the impurities are filtered off, the pH is adjusted to 3, the mixture is cooled, filtered and the precipitate is dried. 5.1 g of 2-cyanimino-3-(2-hydroxy-5-nitro-benzyl)-thiazolidine are obtained, melting at 253° to 255° C. after crystallization from pyridine.

Analysis for $C_{11}H_{10}N_4O_3S$ (278.29): calculated: C 47.47%, H 3.62%, N 20.13%; found: C 47.78%, H 3.71%, N 20.01%.

IR spectrum (KBr): 3100 cm$^{-1}$ (broad) —OH; 2190 cm$^{-1}$ —C≡N—; 1575 cm$^{-1}$ =C=N—; 1522, 1338 cm$^{-1}$ —NO$_2$.

NMR spectrum (CDCl$_3$+DMSO-d$_6$): 3.4 ppm m(2) —S—CH$_2$—; 3.8 ppm m(2) =N—CH$_2$— (hetrocyclic); 4.54 ppm s(2) =N—CH$_2$— (2—OH, 5—NO$_2$— C$_6$H$_3$); 6.88 ppm t(1) —Ar—H(3); 8.00 ppm m(2) —Ar—H(4.6); 5–9 ppm b(1) —OH.

EXAMPLE 6

2-Cyanimino-3-(3-hydroxybenzyl)-thiazolidine 3.82 g (30 mmoles) of 2-cyanimino-thiazolidine, 7.10 g (30 mmoles) of m-cresyl-bromide acetate and 4.30 g of anhydrous potassium carbonate are boiled in 100 ml of acetone for 6 hours. The precipitate is filtered off and the filtrate is evaporated to dryness. 8.75 g of an oily material are obtained, which is hydrolyzed with 50 ml of 2N sodium hydroxide to eliminate the phenylester group. Upon acidification again an oily product precipitates, which is recrystallized from acetonitrile and subsequently 50% acetone to yield 1.98 g of 2-cyanimino-3-(3-hydroxybenzyl)-thiazolidine, melting at 126° to 128° C.

Analysis for $C_{11}H_{11}N_3OS$ (233.29): calculated: C 56.63%, H 4.75%, S 13.75%, N 18.02%; found: C 56.70%, H 5.07%, S 13.75%, N 17.83%.

IR spectrum (KBr): 3260, 1230 cm$^{-1}$ —OH; 2190 cm$^{-1}$ —C≡N; 1570 cm$^{-1}$ =C=N—.

NMR spectrum (CDCl$_3$+DMSO-d$_6$): 3.3 ppm m(2) —S—CH$_2$—; 3.7 ppm m(2) =N—CH$_2$— (heterocyclic); 4.48 ppm s(2) =N—CH$_2$— (hydroxyphenyl); 6.5–7.4 ppm m(4) —Ar—H; 8.6 b(1) —OH.

EXAMPLE 7

2-Cyanimino-3-(1-napthylmethyl)-thiazolidine 3.82 g (30 moles) of 2-cyaniminothiazolidine, 5.56 g (30 mmoles) of 1-chloromethyl-naphthalene and 4.3 g of potassium carbonate are boiled in 100 ml of acetone for 6 hours. The precipitate is filtered off while hot; 6 parts of the product precipitates already during filtration. After concentration and storage in a refrigerator 6.5 g (81.15%) of 2-cyanimino-3-(1-naphthylmethyl)-thiazolidine are obtained, melting at 167° C. after recrystallization from acetonitrile.

Analysis for $C_{15}H_{13}N_3S$ (267.34): calculated: C 67.39%, H 4.90%, N 15.72%, S 12.00%; found: C 67.32%, H 4.80%, N 15.78%, S 11.96%.

IR spectrum (KBr): 2190 cm$^{-1}$ —C≡N; 1580 cm$^{-1}$ =C=N—.

NMR spectrum (CDCl$_3$+DMSO-d$_6$): 3.2 ppm m(2) —S—CH$_2$—; 3.6 ppm m(2) =N—CH$_2$— (heterocyclic); 4.92 ppm s(2) =N—CH$_2$— (naphthyl); 7.0–7.9 ppm m(7) —Ar—H.

EXAMPLE 8

3,3'-(1,4-Xylylene)-bis(2-cyanimino-thiazolidine)

4.5 g (26 mmoles) of 1,4-xylylene dichloride, 6.36 g (50 mmoles) of 2-cyanimino-thiazolidine and 7.17 g of potassium carbonate are boiled in 150 ml of acetone for 7 hours, the mixture is put into a refrigerator and filtered after cooling. 15.48 g of a precipitate are filtered off, from which the inorganic impurities are dissolved with cold water. 8.1 g (91%) of the named compound are obtained, melting at 275° to 278° C. after recrystallization from 70 ml of dimethyl formamide.

Analysis for $C_{16}H_{16}N_6S_2$ (356.47): calculated: C 53.91%, H 4.52%, S 17.99%, N 23.58%; found: C 53.70%, H 4.78%, S 17.85%, N 23.37%.

IR spectrum (KBr): 2180 cm$^{-1}$ -C≡N; 1570 cm$^{-1}$ =C=N—.

NMR spectrum (DMSO-d$_6$): 3.4 ppm m(4) —S—CH$_2$—; 3.7 ppm m(4) =N—CH$_2$— (heterocyclic); 4.50 ppm S(4) =N—CH$_2$— (phenylene); 7.18 ppm S(4) —Ar—H.

EXAMPLE 9

2-Cyanimino-3-(6-methyl-2-pyridylmethyl)-thiazolidine or
2-[(2-cyanimino-3-thiazolinyl)-methyl]-6-methyl-pyridine 3.3 g (26 moles) of 2-cyanimino-thiazolidine, 3.9 g of anhydrous potassium carbonate and 4.03 g (28.5 moles) of 2-chloromethyl-6-methyl-pyridine in 60 ml of acetone are boiled until the total amount of the starting thiazolidine compound is used up (6 hours). The precipitated salt is filtered off, the solvent is distilled off and the residue is crystallized from 40 ml of diethyl ether. 5.43 g (89.9%) of the named compound are obtained, melting at 114° C. after crystallization from ethyl acetate.

Analysis for $C_{11}H_{12}N_4S$ (232.30): calculated: C 56.87%, H 5.20%, N 24.12%; found: C 56.77%, H 5.12%, N 24.18%.

IR spectrum (KBr): 21.90 cm$^{-1}$ —C≡N; 1570 cm$^{-1}$ =C=N—.

NMR spectrum (CDCl₃): 2.48 ppm s(3) —Py—CH₃; 3.3 ppm m(2) —S—CH₂—; 3.9 ppm m(2) =N—CH₂—; 4.60 ppm s(2) =N—CH₂— (Py); 6.9 ppm d(2) —Py 2.5—H; 7.4 ppm 6(1) —Py4—H.

EXAMPLE 10

2-Cyanimino-3-(6-dichloromethyl-2-pyridylmethyl)-thiazolidine or

2-[(2-cyanimino-3-thiazolinyl)-methyl]-6-dichloromethyl pyridine 6.6 g (52 moles) of 2-cyanimino-thiazolidine, 7.9 g of anhydrous potassium carbonate and 12 g (57 mmoles) of 2-dichloromethyl-6-chloromethyl-pyridine in 240 ml of acetone are reacted as described in the previous examples. The precipitated salt is filtered off, the evaporation residue released from the solvent is triturated with ether, filtered and crystallized from acetonitrile to yield 5.2 g (33%) of the named compound, melting at 122° C.

Analysis for $C_{11}H_{10}Cl_2N_4S$ (301.19): calculated: C 43.86%, H 3.34%, S 10.64%; found: C 43.91%, H 3.46%, S 10.80%.

IR spectrum (KBr): 2180 cm⁻¹ —C≡—N—; 1560 cm⁻¹ =CH—Cl.

NMR spectrum (CDCl₃): 3.34 ppm t(2) —S—CH₂—; 3.97 ppm t(2) =N—CH₂—; 4.62 ppm s(2) =N—CH₂— (phenyl); 6.50 ppm s(1) —Py—CH=; 7.0–7.8 ppm m(3) —Py—H.

EXAMPLE 11

3-Benzyl-2-(carbamoylimino)-thiazolidine 6.36 g (50 moles) of 3-benzyl-2-cyanimino-thiazolidine are boiled with 80 ml of a 10% hydrochloric acid for 10 minutes. A clear solution is obtained, which is cooled down and alkalized with a 25% aqueous ammonium hydroxide solution to yield 5.65 g of 3-benzyl-2-carbamoylimino-thiazolidine, melting at 143° to 145° C. After crystallization from ethanol the melting point is raised to 148° C.

Analysis for $C_{11}H_{13}N_3OS$ (235.31): calculated: C 56.15%, H 5.57%, N 17.86%; found: C 56.10%, H 5.46%, N 18.10.

IR spectrum (KBr): 3320, 3260 cm⁻¹ —NH₂; 1645 cm⁻¹ =C=O; 1540 cm⁻¹ =C=N—.

NMR spectrum (CDCl₃+DMSO-d₆): 3.05 ppm t(2) —S—CH₂—; 3.5 ppm t(2) =N—CH₂— (heterocyclic); 4.75 ppm s(2) =N—CH₂— (phenyl); 5.6 ppm b(2) —NH₂; 7.32 ppm s(5) —Ar—H.

EXAMPLE 12

3-Benzyl-2-nitromethylene-thiazolidine 3.34 g (20 moles) of N-benzyl-cysteamine and 3.3 g of 1,1-bis-methylthio-2-nitro-ethylene are refluxed in 50 ml of ethanol for one hour. The gas evolution terminates after boiling for 20 minutes. The mixture is cooled and the precipitated product is isolated by filtration. 4.52 g of 3-benzyl-2-nitromethylene-thiazolidine are obtained, melting at 136° to 138° C. Crystallization of the product from 140 ml of ethanol yields 4.08 g of a purified product, melting at 139° C.

Analysis for $C_{11}H_{12}N_2O_2S$ (236.30): calculated: C 55.91%, H 5.12%, N 11.86%; found: C 55.81%, H 4.99%, N 11.89%.

IR spectrum (KBr): 1633 cm⁻¹ =C=C=; 1535, 1354 cm⁻¹ —NO₂.

NMR spectrum (CDCl₃): 3.1 ppm t —S—CH₂—; 3.8 ppm t =N—CH₂— (heterocyclic); 4.43 ppm s =N—CH₂— (C₆H₅); 6.97 ppm s —CH=; 7.0–7.3 ppm m —Ar—H.

EXAMPLE 13

2-Cyanimino-3-(4-methoxybenzyl)-thiazolidine 3.65 g (23.5 moles) of cyanimino-dithiocarbonic acid dimethylester (purity: 94%) and 5.91 (30 moles) of N-(4-methoxybenzyl)-cysteamine are boiled in 30 ml of ethanol until the evolution of methyl mercaptan terminates. The reaction mixture is evaporated and the crystalline residue is recrystallized from 15 ml of isopropanol. 5.35 g (92%) of 2-cyanimino-3-(4-methoxybenzyl)-thiazolidine are obtained, melting at 99° to 102° C.

Analysis for $C_{12}H_{13}N_3OS$ (247.31): calculated: C 58.28%, H 5.30%; found: C 58.35%, H 5.17%;

IR spectrum (KBr): 2840 cm⁻¹ —O—CH₃; 2185 cm⁻¹ —C≡—N; 1570 cm⁻¹ =C=N—; 1608, 814 cm⁻¹ —Ar.

NMR spectrum (CDCl₃): 3.3 ppm m —S—CH₂—; 3.7 ppm m =N—CH₂—; 3.75 ppm s —O—CH₃; 4.43 ppm s =N—CH₂— (C₆H₅); 6.9 ppm q —Ar—H.

The N-(4-methoxybenzyl)-cysteamine used as a starting material is prepared by reacting 4-methoxy-benzaldehyde with cysteamine and reducing the 2-(4-methoxyphenyl)-thiazolidine (m.p. 93°–94° C. after crystallization from isopropanol) obtained with sodium borohydride in isopropanol [J. Org. Chem. 27, 4712 (1962)]. N-(4-methoxybenzyl)-cysteamine is an oil boiling at 120°–125° C./0.4 mmHg.

EXAMPLE 14

2-Cyanimino-3-(2-furylmethyl)-thiazolidine 1.82 g (11.8 mmoles) of cyanimino-dithiocarbonic acid dimethylester (purity: 94%) and 2.36 g (15 mmoles) of N-(2-furylmethyl)-cysteamine are refluxed in 20 ml of ethanol for 2 hours (the evolution of methyl mercaptan ceases after 70 minutes). The reaction mixture is evaporated and the solid residue is crystallized from 8 ml of isopropanol. 1.98 g (87.5%) of the named compound are obtained, melting at 124° to 125° C.

Analysis for $C_9H_9N_3OS$ (207.25): calculated: N 20.28%, S 15.47%; found: N 20.38%, S 15.44%.

IR spectrum (KBr): 2185 cm⁻¹ —C≡—N; 1570 cm⁻¹ =C=N—; 1238 cm⁻¹ =C—O—C=; 795 cm⁻¹ —Ar—H.

NMR spectrum (CDCl₃): 3.3 ppm m —S—CH₂—; 3.7 ppm m =N—CH₂—(heterocyclic); 4.57 ppm s =N—CH₂—Ar; 6.3 ppm d —Ar(3,4)H; 7.3 ppm m —Ar(5)H.

H-2(furylmethyl)-cysteamine has been prepared following the procedure described in Example 13, by reducing 2-(2-furyl)-thiazolidine with sodium borohydride. Boiling point: 72° to 75° C./0.3 mmHg.

EXAMPLE 15

2-Cyanimino-3-(4-methylbenzyl)-thiazolidine 3.65 g (23.5 mmoles) of cyanimino-dithiocarbonic acid dimethylester (purity: 94%) and 5.43 g (30 mmoles) of N-(4-methylbenzyl)-cysteamine are boiled in 30 ml of ethanol until the evolution of methyl-mercaptan terminates (about 2 hours). The reaction mixture is evaporated and the crystalline residue is recrystallized from 6 ml of isopropanol. 4.65 g (85.5%) of 2-cyanimino-N-(4-methylbenzyl)-thiazolidine are obtained, melting at 102° to 104° C.

Analysis for $C_{12}H_{13}N_3S$ (231.31): calculated: C 62.26%, H 5.66%, S 13.85%; found: C 62.16%, H 5.52%, S 13.96%.

IR spectrum (KBr): 2190 cm$^{-1}$ —C≡—N; 1590 cm$^{-1}$ =C=N—; 1260 cm$^{-1}$ —S—CH$_2$—; 792 cm$^{-1}$ —Ar.

NMR spectrum (CDCl$_3$): 2.31 ppm s —CH$_3$; 3.3 ppm m —S—CH$_2$—; 3.7 ppm m =N—CH$_2$—(heterocyclic); 4.54 ppm s =N—CH$_2$—(phenylene); 7.10 ppm s —Ar—H.

N-(4-methylbenzyl)-cysteamine used as a starting material is prepared according to J. Org. Chem. 27, 4712 (1962): 2-(4-methylphenyl)-thiazolidine (m.p. 92° to 93° C. after recrystallization from isopropanol) obtained by reacting 4-methyl-benzaldehyde with cysteamine is reduced with sodium borohydride in isopropanol N-(4-methyl-benzyl)-cysteamine is an oily product which has a boiling point of 96° to 98° C./0.2 mmHg.

EXAMPLE 16

3-(2-Furyl-methyl)-2-nitromethylene-thiazolidine 3.82 g (24.3 mmoles) of N-(2-furyl-methyl)-cysteamine and 4 g (24.2 mmoles) of 1,1-bis-methylthio-2-nitor-ethylene are boiled in 80 ml of ethanol for one and a half hours (the gas evolution terminates in about half an hour). The reaction mixture is allowed to stand in a refrigerator overnight, whereupon the precipitated product is isolated. 4.76 g (86.7%) of 3-(2-furylmethyl)-2-nitromethylene-thiazolidine are obtained, melting at 190°-192° C. after recrystallization from nitromethane.

IR spectrum (KBr): 1543, 1340 cm$^{-1}$ —NO$_2$; 1640 cm$^{-1}$ =C=C=; 3130, 757 cm$^{-1}$ furan =C—H; 1243 cm$^{-1}$ =C—O—C= furan ring.

NMR spectrum (CH$_3$-COOH): 3.7 ppm t —S—CH$_2$—; 4.6 ppm t —N—CH$_2$—; 5.7 ppm s >N—CH$_2$—(C$_4$H$_3$O); 6.3 ppm b =CH—NO$_2$; 6.5 ppm m furan 3.4H; 7.5 ppm n furan 5H.

EXAMPLE 17

2-Cyanimino-3-(4-hydroxy-benzyl)-thiazolidine 0.49 g (2 moles) of 2-cyanimino-3-(4-methoxybenzyl)-thiazolidine are dissolved in 12 ml of dichloromethane and a solution of 3.01 g (1.14 ml, 13 mmoles) of borotribromide in 5 ml of dichloromethane is added in an argon atmosphere, dropwise. The mixture is stirred for 12 hours and is then alkalized with an aqueous ammonium hydroxide solution, under stirring and cooling. The phases are separated and the organic phase is evaporated. 0.22 g of 2-cyanimino-3-(4-hydroxy-benzyl)-thiazolidine are obtained in a white crystalline form, melting at 175° to 177° C.

IR spectrum (KBr): 2190 cm$^{-1}$ —C=C≡N; 1570 cm$^{-1}$ =C=N—; 3210 cm$^{-1}$ —OH; 1610, 840 cm$^{-1}$ —Ar.

NMR spectrum (CDCl$_3$): 3.4 ppm m —S—CH$_2$—; 3.7 ppm m =N—CH$_2$—; 4.5 ppm s —Ar—CH$_2$—; 6.9 ppm q —Ar—H; 9.47 ppm s —CH.

EXAMPLE 18

Preparation of a pharmaceutical composition

A pharmaceutical composition formulated in the form of tablets is prepared from the following ingredients (pro 1000 tablets):

| | |
|---|---|
| 50 g | of 3-benzyl-2-cyanimino-thiazoline (active ingredient) |
| 75 g | of starch |
| 55 g | of milk sugar |
| 10 g | of talc |
| 6 g | of polyvinyl-pyrrolidone |
| 3 g | of magnesium stearate |
| 1 g | of colloidal silicic acid |
| 200 g. | |

The finely ground active ingredient is admixed with the milk sugar and talc, the mixture obtained is pulpified with the polyvinyl-pyrrolidone solution and passes through a screen. The granules are dried and admixed with magnesium stearate and colloidal silicic acid, whereupon the mixture is pressed into 100 pieces of tablets, weighing 0.2 g each.

We claim:

1. A thiazolidine of the formula (I)

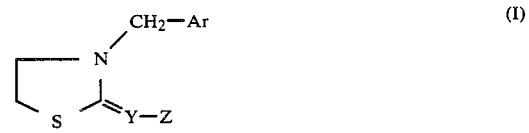

wherein

Ar is a 2-furyl or phenyl, naphthyl or pyridyl group which can be substituted by one or more of $C_{1-4}$-alkyl, $C_{1-6}$-alkoxy, halo-$C_{1-4}$ alkoxy, di- or trihalomethyl, hydroxyl or nitro or by a group of the formula (II)

wherein

Y is nitrogen or CH,

Z is cyano when Y is nitrogen, and is nitro when Y is CH.

2. 3-Benzyl-2-cyanimino-thiazolidine.

3. 3-benzyl-2-nitromethylene-thiazolidine.

4. A pharmaceutical composition for treating a gastrointestinal ulcer, which comprises as an active ingredient a pharmaceutically effective amount of at least one compound of the formula (I) as defined in claim 1 in admixture with a pharmaceutically acceptable inert carrier.

5. The pharmaceutical composition for treating a gastrointestinal ulcer as claimed in claim 3 in the form of a formulation suitable for oral administration.

6. A method of treating a gastrointestinal ulcer in an animal subject afflicted with said gastrointestinal ulcer, which comprises the step of administering to said animal subject a pharmaceutically effective amount of a compound of the formula (I) as defined in claim 1.

7. A method of treating a gastrointestinal ulcer in an animal subject afflicted with said gastrointestinal ulcer, which comprises the step of administering to said animal subject a pharmaceutically effective amount of a compound of the Formula (I)

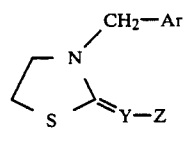 (I)
wherein
Ar is 2-furyl or phenyl, naphthyl or pyridyl which can be substituted by one or more of $C_1$–$C_4$ alkoxy, halo-$C_1$ to $C_4$ alkoxy, di- or trihalomethyl, hydroxyl or nitro, or by a group of the Formula (II)
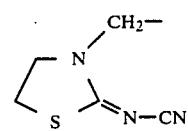 (II)
wherein
Y is nitrogen or CH;
Z is cyano or carbamoyl when Y is nitrogen, and is nitro when Y is CH.
* * * * *